US012620106B2

(12) United States Patent
Stein et al.

(10) Patent No.: US 12,620,106 B2
(45) Date of Patent: May 5, 2026

(54) MRI-BASED TEXTURAL ANALYSIS OF TRABECULAR BONE

(71) Applicant: New York Society for the Relief of the Ruptured and Crippled, maintaining the Hospital for Special Surgery, New York, NY (US)

(72) Inventors: Emily M. Stein, New York, NY (US); Ryan Breighner, New York, NY (US); Matthew F. Koff, Livingston, NJ (US)

(73) Assignee: NEW YORK SOCIETY FOR THE RELIEF OF THE RUPTURED AND CRIPPLED, MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 673 days.

(21) Appl. No.: 17/914,889

(22) PCT Filed: Mar. 31, 2021

(86) PCT No.: PCT/US2021/025179
§ 371 (c)(1),
(2) Date: Sep. 27, 2022

(87) PCT Pub. No.: WO2021/202738
PCT Pub. Date: Oct. 7, 2021

(65) Prior Publication Data
US 2023/0134785 A1     May 4, 2023

Related U.S. Application Data

(60) Provisional application No. 63/004,908, filed on Apr. 3, 2020.

(51) Int. Cl.
*G06T 7/40* (2017.01)
*A61B 5/00* (2006.01)
(Continued)

(52) U.S. Cl.
CPC ................ *G06T 7/40* (2013.01); *A61B 5/055* (2013.01); *A61B 5/4509* (2013.01);
(Continued)

(58) Field of Classification Search
CPC ....... A61B 34/10; A61B 5/055; A61B 5/4504; A61B 5/4509; A61B 5/7275;
(Continued)

(56) References Cited

U.S. PATENT DOCUMENTS 6,205,348 B1     3/2001   Giger et al.
6,725,082 B2     4/2004   Sati et al.
(Continued)

OTHER PUBLICATIONS

Haralick et al., "Chapter 11 Statistical Image Texture Analysis," Handbook of Pattern Recognition and Image Processing, Jan. 1, 1986, pp. 247-279, retrieved from <URL:https://haralick.org/book_chapters/Statistical_Image_Texture.pdf>.
(Continued)

*Primary Examiner* — Kenny A Cese
(74) *Attorney, Agent, or Firm* — Fish & Richardson P.C.

(57) ABSTRACT

In an example method, a computer system receives one or more images of one or more bones of a patient. The one or more images are generated by a magnetic resonance imaging (MRI). The computer system determines one or more metrics indicative of an image texture of the one or more images; and determines at least one of a bone risk or a bone health of the patient based on the one or more metrics.

13 Claims, 5 Drawing Sheets

(51) Int. Cl.

| | |
|---|---|
| *A61B 5/055* | (2006.01) |
| *A61B 34/10* | (2016.01) |
| *G06T 7/00* | (2017.01) |

(52) U.S. Cl.
CPC ............ *A61B 5/7275* (2013.01); *A61B 34/10* (2016.02); *G06T 7/0012* (2013.01); *G06T 2207/10088* (2013.01); *G06T 2207/30008* (2013.01)

(58) Field of Classification Search
CPC . G06T 2207/10088; G06T 2207/20076; G06T 2207/30008; G06T 2207/30012; G06T 7/0012; G06T 7/40; G06T 7/41; G06T 7/45

See application file for complete search history.

(56) References Cited

U.S. PATENT DOCUMENTS

| | | | |
|---|---|---|---|
| 7,664,542 | B2 | 2/2010 | Boese et al. |
| 8,126,239 | B2 | 2/2012 | Sun et al. |
| 9,092,691 | B1 * | 7/2015 | Beaumont .............. G06V 10/25 |
| 9,757,202 | B2 | 9/2017 | Chen et al. |
| 2003/0133601 | A1 | 7/2003 | Giger et al. |
| 2007/0111933 | A1 | 5/2007 | Kopchick et al. |
| 2011/0243416 | A1 | 10/2011 | Gregory et al. |
| 2013/0204115 | A1 * | 8/2013 | Dam .......................... G06T 7/44 600/410 |
| 2016/0262686 | A1 * | 9/2016 | Tsuji ................... A61B 5/7278 |
| 2017/0202520 | A1 | 7/2017 | Urish et al. |
| 2018/0192910 | A1 | 7/2018 | Claude et al. |
| 2018/0303409 | A1 | 10/2018 | Tsuji et al. |
| 2019/0216452 | A1 | 7/2019 | Nawana et al. |
| 2019/0310338 | A1 | 10/2019 | James et al. |
| 2019/0388123 | A1 * | 12/2019 | Pavlovskaia ............ G06T 19/00 |
| 2020/0069257 | A1 * | 3/2020 | Fleming ................ G06T 11/005 |
| 2024/0206990 | A1 * | 6/2024 | Boddington ......... G06V 10/426 |

OTHER PUBLICATIONS

Office Action in European Appln. No. 21780534.0, mailed on Dec. 18, 2024, 7 pages.
Areeckal et al. "Current and Emerging Diagnostic Imaging-Based Techniques for Assessment of Osteoporosis and Fracture Risk," IEEE Reviews in Biomedical Engineering, 2019, vol. 12, pp. 254-268.
Extended European Search Report in European Appln. No. 21780534.0, mailed on Mar. 28, 2024, 10 pages.
Khan et al., "Application of Image Processing in Detection of Bone Diseases Using X-rays," Pattern Recognition and Image Analysis, 2020, 30(1):97-107.
Office Action in Canadian Appln. No. 3172636, mailed on Dec. 3, 2024, 16 pages.
Office Action in Canadian Appln. No. 3172636, mailed on Jan. 4, 2024, 4 pages.
Cheah et al., "MRI-based textural analysis of trabecular bone: a novel method for opportunistic screening of bone quality," JBMR, Dec. 2019, 34(S1):97-98.
Cheah et al., "MRI-based Textural Analysis of Trabecular Bone: A Novel Method for the Opportunistic Screening of Bone Quality," Abstract No. 2206, Presented at 2019 American College of Rheumatology/The Association of Rheumatology Professionals (ACR/ARP) Annual Meeting, Atlanta, Georgia, USA, Nov. 8-13, 2019; Arthritis Rheumatol. 2019, 71 (suppl 10), 2 pages.
International Preliminary Report on Patentability in International Appln. No. PCT/US2020/051557, dated Oct. 13, 2022, 6 pages.
International Preliminary Report on Patentability in International Appln. No. PCT/US2021/025179, dated Oct. 13, 2022, 13 pages.
International Search Report and Written Opinion in International Appln. No. PCT/US2020/051557, dated Dec. 3, 2020, 7 pages.
International Search Report and Written Opinion in International Appln. No. PCT/US2021/025179, dated Jul. 12, 2021, 14 pages.
Koff et al., "MRI Based Textural Analysis of Trabecular Bone: A Novel Method For Opportunistic Screening of Bone Quality," Abstract, Paper No. 1296, Orthopaedic Research Society 2020 Annual Meeting, Phoenix, Arizona, USA, Feb. 8-11, 2020, 1 page.

\* cited by examiner

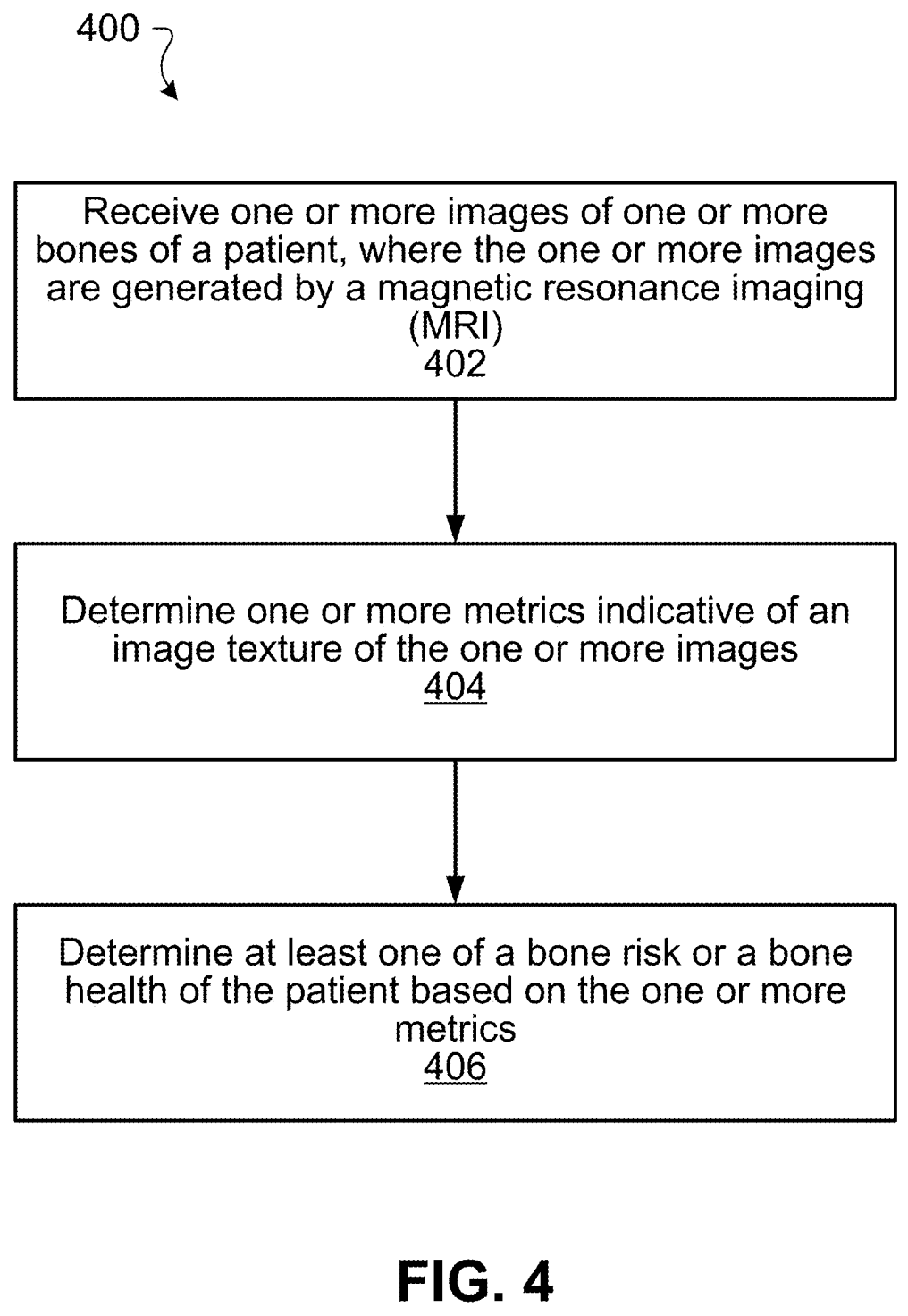

400

Receive one or more images of one or more
bones of a patient, where the one or more images
are generated by a magnetic resonance imaging
(MRI)
402

Determine one or more metrics indicative of an
image texture of the one or more images
404

Determine at least one of a bone risk or a bone
health of the patient based on the one or more
metrics
406

FIG. 4

MRI-BASED TEXTURAL ANALYSIS OF TRABECULAR BONE

CROSS-REFERENCE TO RELATED APPLICATIONS

This application is a National Stage application under 35 U.S.C. § 371 of international Application No. PCT/US2021/025179, having an International Filing Date of Mar. 31, 2021, which claims priority to U.S. Provisional Patent Application No. 63/004,908, filed Apr. 3, 2021, the entire content of which is incorporated herein by reference.

FIELD OF THE TECHNOLOGY

The present technology relates to magnetic resonance imaging (MRI) and measurement of bone properties.

BACKGROUND

Osteoporosis and fragility fracture are extremely prevalent, and associated with significant morbidity, mortality and health care costs. However, osteoporosis is often overlooked, even among high risk individuals, leading to missed treatment opportunities. In North America, it has been estimated that up to 80% of individuals who sustain a fragility fracture are never evaluated or treated for osteoporosis. Bone mineral density (BMD) measured by dual energy x-ray absorptiometry (DXA) is the gold standard for diagnosis of osteoporosis. However, several structural and material properties beyond BMD independently contribute to overall fracture risk.

Several techniques are currently available to measure different attributes of bone quality including high resolution peripheral quantitative computed tomography (QCT), central QCT, bone biopsy, high-resolution magnetic resonance imaging (MRI), and reference point indentation. However, these methods must be performed prospectively, limiting their application for screening. Trabecular bone score (TBS) is a DXA-derived technique currently used in clinical practice. This textural measurement derived from lumbar spine DXA images is able to discern attributes of trabecular microarchitecture based on trabecular bone distribution, and can discriminate and predict fracture independently of BMD.

DXA is currently under-utilized in the assessment of osteoporosis as many high-risk patients are never screened. Opportunistic methods, using imaging obtained for other clinical purposes, are needed for the identification of individuals at risk for osteoporosis.

SUMMARY

In an aspect, a method includes receiving, by a computer system, one or more images of one or more bones of a patient, where the one or more images are generated by a magnetic resonance imaging (MRI); determining, by a computer system, one or more metrics indicative of an image texture of the one or more images, where the one or more metrics includes an inverse difference moment associated with the one or more images; and determining, by the computer system, at least one of a bone risk or a bone health of the patient based on the one or more metrics.

Implementations of this aspect can include one or more of the following features.

In some implementations, the one or more bones can include trabecular bone.

In some implementations, the one or more bones can include at least one of a vertebra, a radius, a pelvis, a femur, a tibia, a rib, or a clavicle.

In some implementations, determining at least one of the bone risk or the bone health of the patient can include determining a bone fracture risk for the patient.

In some implementations, determining at least one of the bone risk or the bone health of the patient can include determining a disorder associated with the one or more bones.

In some implementations, determining at least one of the bone risk or the bone health of the patient can include determining that patient suffers from osteoporosis.

In some implementations, determining at least one of the bone risk or the bone health of the patient can include determining a risk of complications associated an orthopedic procedure.

In some implementations, determining at least one of the bone risk or the bone health of the patient can include determining a likelihood of success associated with an orthopedic procedure.

In some implementations, determining the one or more metrics indicative of the image texture of the one or more images can include determining a heterogeneity of the one or more images.

In some implementations, the one or more metrics can further include an angular second moment associated with the one or more images.

In some implementations, the one or more metrics can further include an entropy associated with the one or more images.

In some implementations, the one or more metrics can further include at least one of: an energy of the one or more images, a contrast of the one or more images, a homogeneity of the one or more images, an autocorrelation of the one or more images, a correlation of the one or more images, a cluster shade of the one or more images, a histogram of the one or more images, a mean of the one or more images, a variance of the one or more images, a skewness of the one or more images, an absolute gradient of the one or more images, a gradient mean of the one or more images, a gradient variance of the one or more images, a gradient skewness of the one or more images, a gradient kurtosis of the one or more images, a proportion of pixels with non-zero gradient of the one or more images, a run length matrix of the one or more images, a short run length matrix of the one or more images, a long run length matrix of the one or more images, a run length non-uniformity of the one or more images, a gray level non-uniformity of the one or more images, and/or fraction run of the one or more images.

In some implementations, each of the one or more metrics can be associated with a spatial direction.

In some implementations each of the one or more metrics can be associated with a plurality of spatial directions.

In some implementations, each of the spatial directions can be a respective diagonal direction expressed according to a cubic kernel.

In some implementations the plurality of spatial directions can include four diagonal directions expressed according to a cubic kernel.

The details of one or more implementations of the technologies described herein are set forth in the accompanying drawings and the description below. Other features, aspects, and advantages of the disclosed technologies will become apparent from the description, the drawings, and the claims.

BRIEF DESCRIPTION OF THE FIGURES

FIG. 4 is a flow chart diagram of an example process for determining a bone risk or a bone health of the patient using MRI.

Like elements in different figures are identified with the same reference numeral.

DETAILED DESCRIPTION

Overview

Figure 1:
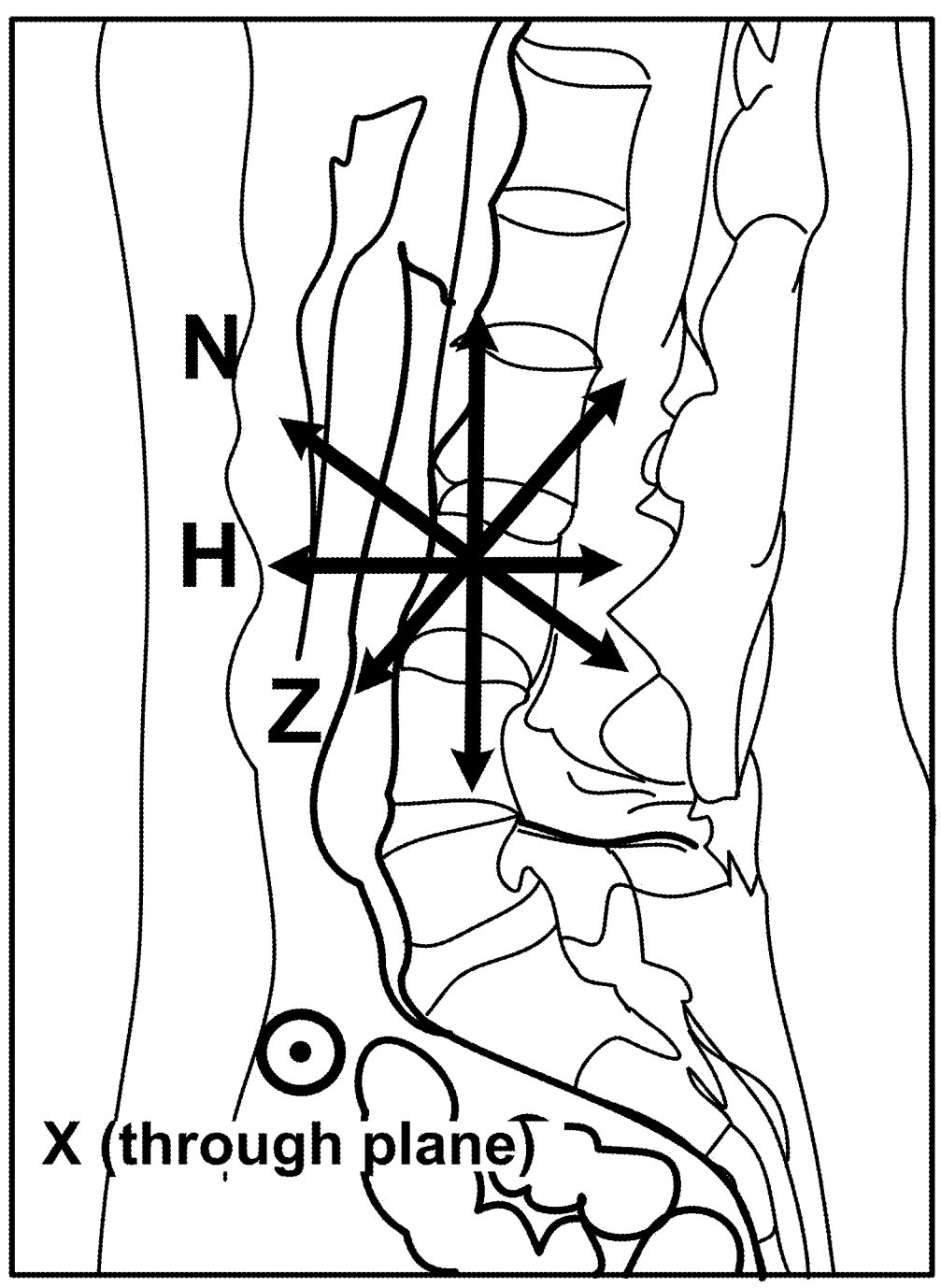
FIG. 1 is a diagram showing anatomic directions for which each texture parameter was calculated. H: horizontal, V: vertical, Z: right-diagonal, N: left-diagonal, X: through plane.

Many individuals at high risk for osteoporosis and fragility fracture are never screened by traditional methods. Opportunistic use of imaging obtained for other clinical purposes is required to foster identification of these individuals. The aim of these pilot studies was to investigate texture analysis of magnetic resonance imaging (MRI) scans as a measure of bone quality.

A first study retrospectively investigated 30 subjects who had lumbar spine MRI performed at our institution. Cases (n=15) were postmenopausal women with osteoporosis and a confirmed history of fragility fracture. Controls (n=15) were healthy women aged 25-35 years.

A second study retrospectively investigated 100 subjects who had lumbar spine MRI performed at our institution. Cases (n=50) were postmenopausal women with osteoporosis and a confirmed history of fragility fracture. Controls (n=50) were age and race matched postmenopausal women with no known fracture history.

In both studies, trabecular bone from the lumbar vertebrae was segmented to create regions of interest within which a gray level co-occurrence matrix was created to quantify the distribution and spatial organization of voxel intensity. Heterogeneity in the trabecular bone texture was assessed by several independent parameters, including: contrast (variability), entropy (disorder) and angular second moment (homogeneity).

In the first study, textural analysis of trabecular bone differentiated between patients with known osteoporotic fractures and controls. Specifically, Trabecular bone in fracture patients had greater microarchitectural variability (+139% contrast), greater disorder (+14% entropy), and was less homogeneous (−60% angular second moment) compared to controls (all p<0.05). Among osteoporosis patients, lower DXA based TBS measurements were associated with greater microarchitectural variability (contrast: r=−0.75 and entropy: r=−0.78) and less homogeneity (r=0.75; p<0.05 for all).

In the second study, texture analysis revealed that trabecular bone was more heterogeneous in fracture patients. Specifically, fracture patients had greater texture variability (+76% contrast), greater disorder (+10% entropy), and less homogeneity (−50% angular second moment) compared to controls (all p<0.05).

Further investigation can be performed to validate this methodology, which has the potential to greatly expand the number of patients screened for skeletal fragility.

Textural Analysis of Trabecular Bone

In both studies, sagittal T1-weighted MR images were acquired using our institutional scanning protocol, with the parameters: echo time (TE)/repetition time (TR): =6.6-24 ms/400-695 ms; receiver bandwidth=81.4-390.6 Hz/pixel; flip angle=90-160°; field-of-view=26-29 cm; acquisition matrix: frequency encodes 320 to 512, phase encodes: 224 to 256.

In the first study, the majority of scans (28/30, 93%) were acquired on clinical 1.5T scanners (GE Healthcare, Waukesha, WI). Two image sets were acquired on a clinical 3T scanners.

In the second study, the majority of scans (88/100) were acquired on clinical 1.5T scanners (GE Healthcare, Waukesha, WI). Twelve image sets were acquired on a clinical 3T scanners.

In both studies, standard patient positioning, and a multichannel head-neck-spine (HNS) or cervical-thoracic-lumbar (CTL) coil was used in the acquisition of all images. Images were then imported into an open-source segmentation program (ITK-SNAP) and the trabecular bone of each lumbar vertebrae were manually segmented to create regions of interest (ROIs) by a single individual. Vertebral bodies with evidence of fracture or prior instrumentation were excluded.

In both studies, next, the source MRI data and the previously segmented ROIs were input into a dedicated texture analysis software (maZda, V18.07), to quantify texture. The image intensity data within the defined ROIs were processed to create a gray level co-occurrence matrix (GLCM) to quantify the distribution and spatial organization of pixel intensity values within the trabecular bone ROI. Subject data were normalized individually to a range defined by the 1st and 99th percentiles of input image voxel intensities within the defined ROIs.

In both studies, the specific texture measures calculated for the image data were: angular second moment (image homogeneity), contrast (image variability), correlation (image linear dependence), entropy (image disorder) and inverse difference moment (image homogeneity). Equations used to calculate these values are detailed in the software manual. The texture measures were calculated in all image directions relative to the image plane: superior/inferior (V), anterior/posterior (H), antero-superior/postero-inferior (N), antero-inferior/postero-superior (Z), and through plane (X), as shown in FIG. 1. Texture calculations were performed using 8 bits per voxel and offset values of 1 to 5 voxels, inclusive. The average value of the texture parameter from all offsets was used the statistical analysis.

Figure 2:
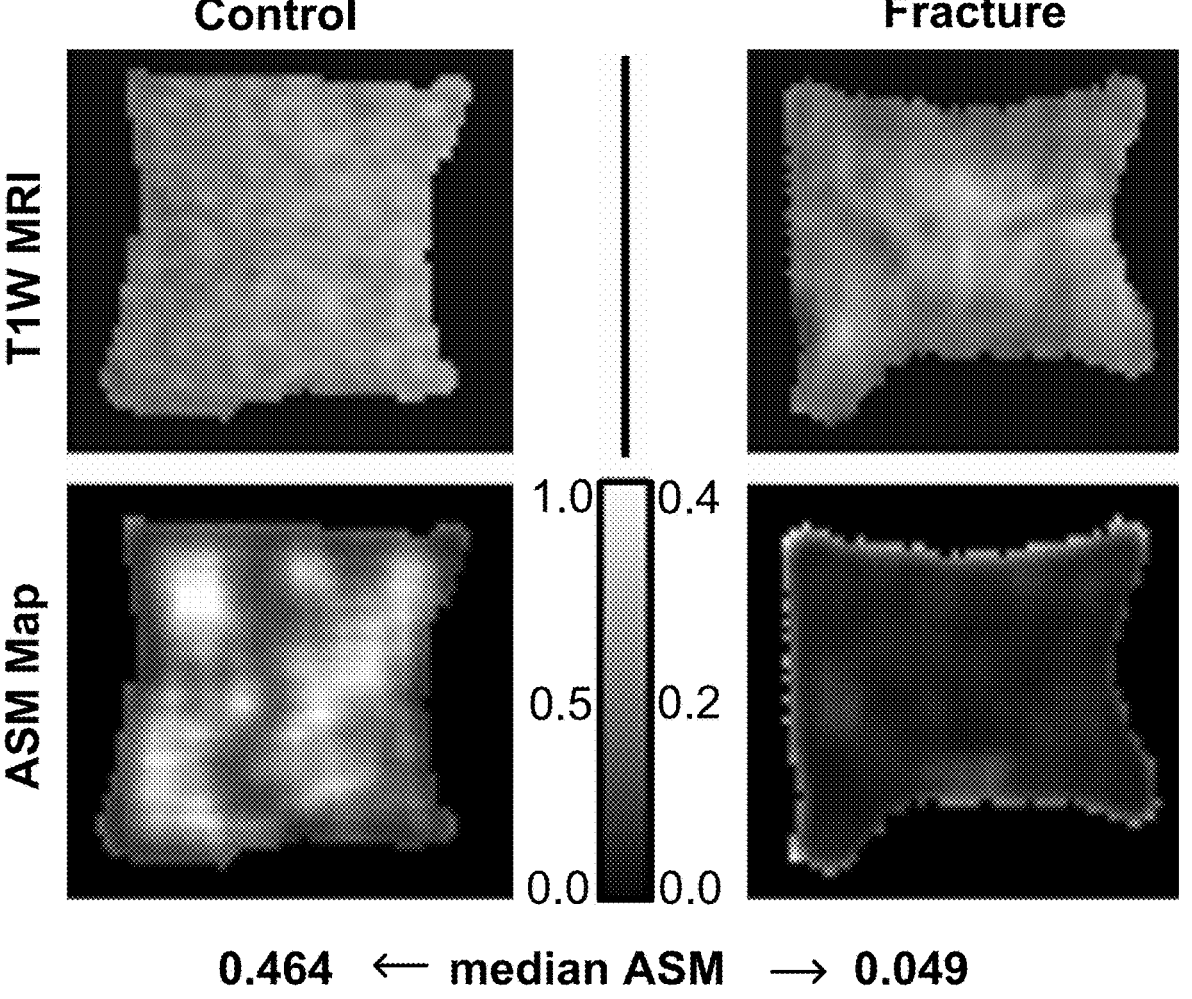
FIG. 2 shows segmented T1-weighted (T1W) MRI and accompanying area second moment (ASM) maps of representative L4 vertebrae from control and fracture groups. T1W images were windowed to span the range of intensities present within the segmented trabecular bone. Higher ASM values indicate greater homogeneity of signal intensity in the source T1W images. ASM was calculated for segmented (trabecular) voxels only. Grayscales of ASM maps intentionally differ to maximize contrast in each map's respective range of local ASM values. Median ASM for each vertebra are provided.

FIG. 2 illustrates the segmented T1-weighted MRI and accompanying area second moment (ASM) maps. The range of signal intensity and corresponding quantification of ASM or homogeneity is depicted for a representative fracture subject and control.

Method Precision

In the second study, inter-rater reliability was calculated by having the images segmented and analyzed by two independent members of the research team. This precision study was performed on 28 subjects in order to achieve 80% power to detect an intraclass correlation coefficient (ICC) of 0.80 against the null ICC of 0.50 using an F-test at a significance level of 0.025. The ICCs (two-way random, absolute agreement model or ICC2.1) for all texture features were 0.97-0.99 with the exception of contrast (0.55).

Statistical Methods

In the first study, texture features were summarized with medians and interquartile ranges (IQR) for each lumbar level and the mean across L1-L5. Distributions were assessed via histograms and box plots and non-parametric tests were used for skewed variables. Differences in texture parameters between patients and controls were estimated using the Hodges-Lehmann estimator with 95% confidence intervals (CIs) and compared using the Wilcoxon rank-sum test. Spearman correlations were used to investigate the relationships between texture features and DXA based TBS. In this first study, adjustment for multiple comparisons was not performed.

In the second study, characteristics and medical history of patients and controls were summarized with means and standard deviations or counts and percentages. Continuous characteristic variables were compared using t-test. Categorical variables were compared using Chi-square test or Fisher's exact text when counts were less than 5. Texture features were summarized with medians and interquartile ranges (IQR) for the mean across L1-L5 calculated. Distributions were assessed via histograms and box plots. Differences in texture features between patients and controls were compared using the Wilcoxon rank-sum test. Area under the ROC curve (AUC) was estimated for each texture feature to assess ability of each to discriminate between fracture cases and controls. From the ROC curves, threshold values based on the Youden's index for the texture features were obtained, with 95% confidence intervals (CIs) for AUC, sensitivity, and specificity estimated from 5000 bootstrap resamples.

In both studies, analyses were performed in SAS version 9.4 (SAS Institute Inc, Cary, NC) and R version 3.4.4 (R Core Team, Vienna, Austria). In this first study, adjustment for multiple comparisons was not performed. A p-value of <0.05 was used to represent statistical significance.

Results

Subjects

In the first study, a total of 30 women were included, 15 cases and 15 controls. All subjects were Caucasian. Cases (mean age 77 years) were postmenopausal women with a confirmed history of fragility fracture as well as an ICD10 diagnosis of osteoporosis. The sites of fragility fracture included vertebrae (10/15), distal radius (2/15), pelvis (2/15), hip (3/15), ribs (1/15), and clavicle (1/15). Five individuals had a history of multiple fractures. The healthy female controls had a mean age of 27 years. These women did not have any chronic medical problems except for back pain which was the indication for their MRI scans.

In the second study, a total of 100 women were included, 50 cases and 50 controls. All subjects were Caucasian. Cases were postmenopausal women with a confirmed history of fragility fracture as well as a diagnosis of osteoporosis (ICD.10 M81.0). Indications for the spine MRI were low back pain or radiculopathy in the majority of women, both fracture cases and controls. Mean age of cases was 74 years, and mean BMI was 23 kg/m². The sites of fragility fracture included vertebrae (33/50), distal radius (13/50), pelvis (11/50), hip (11/50), ribs (7/50), humerus (2/50), ankle (5/50), foot (4/50), and clavicle (1/50). Twenty-two individuals had a history of multiple fractures. The healthy controls had a mean age of 73 years and mean BMI of 27 kg/m². Characteristics of the study subjects, including co-morbidities, medications and supplement use are outlined in Table 1.

TABLE 1

Characteristics of the study population (Second Study).

| | Fracture N = 50 | % | Control N = 50 | % | P-Value* |
|---|---|---|---|---|---|
| Age (mean ± SD) | 74 ± 10 | | 73 ± 10 | | 0.71 |
| BMI (kg/m²; mean ± SD) | 23 ± 4 | | 27 ± 7 | | 0.67 |
| Tobacco use - | | | | | |
| Never (%) | 25 | 50 | 27** | 69 | 0.07 |
| Current or Former (%) | 25 | 50 | 12 | 31 | |
| Cardiovascular Disease (%) | 5 | 10 | 3 | 8 | 0.99 |
| Hyperlipidemia (%) | 2 | 4 | 3 | 8 | 0.66 |
| Hypertension (%) | 14 | 28 | 19 | 49 | 0.05 |
| Type 2 Diabetes (%) | 3 | 6 | 3 | 8 | 0.99 |
| Osteoarthritis (%) | 15 | 30 | 17 | 44 | 0.19 |
| Calcium supplements (%) | 23 | 46 | 6 | 15 | <0.01 |
| Vitamin D supplements (%) | 27 | 54 | 8 | 21 | <0.01 |
| Hormone replacement therapy (%) | 2 | 4 | 1 | 3 | 1.00 |
| Raloxifene (%) | 2 | 4 | 0 | 0 | 0.50 |
| Bisphosphonates (%) | 4 | 8 | 0 | 0 | 0.13 |
| Teriparatide/abaloparatide (%) | 7 | 14 | 0 | 0 | <0.02 |
| Denosumab (%) | 6 | 12 | 0 | 0 | 0.03 |
| Thyroxine (%) | 11 | 22 | 9 | 23 | 0.90 |
| SSRIs (%) | 6 | 12 | 6 | 15 | 0.64 |
| Inhaled glucocorticoids (%) | 3 | 6 | 5 | 13 | 0.29 |
| Proton pump inhibitors (%) | 8 | 16 | 9 | 23 | 0.40 |
| Prior epidural steroids injections (%) | 7 | 14 | 10 | 26 | 0.17 |

*Continuous variables were compared using Wilcoxon signed-rank test. Categorical variables were compared using Chi- square test or Fisher's exact test when counts were less than 5.

Areal BMD by DXA

For both studies, DXA results were available for fracture subjects but not for the healthy controls, for whom no DXA had been performed.

In the first study, among women with fractures, 20% had osteoporosis at the spine, 73% at the total hip or femoral neck. Mean TBS (9 women with values) was 1.290. TBS values were consistent with degraded microarchitecture (<1.200) in 11%, partially degraded (1.200-1.350) in 67%, and normal (>1.350) in 22%.

MRI-Based Analysis of Trabecular Bone Heterogeneity

In the first study, heterogeneity of vertebral trabecular bone (L1-5) was greater among women with fractures when assessed using both the combined and individual anatomic directions. Using the combined values, contrast and entropy measures for which higher values indicate greater heterogeneity, were 139% greater (p<0.04) and 14% greater (p<0.05) in fracture patients, respectively. The mean angular second moment and inverse difference, measures for which lower values indicate greater heterogeneity, were 60% lower (p<0.05) and 30% lower (p<0.05) in fracture patients, respectively (Table 2).

Differences of texture measures between the control and fracture subjects were also detected in the individual anatomic directions. The differences were found between the groups independent of the specific image direction. Contrast was significantly higher in fracture patients compared to controls in all directions assessed (vertical, horizontal, left and right diagonal and through planes). For the other parameters, differences were more pronounced in the vertical (superior/inferior) and through plane (left/right) directions and less pronounced in the horizontal (anterior/posterior) direction.

TABLE 2

Median values for each gray level co-occurrence matrix texture parameter
in individual and combined direction for L1-L5 (first study).

| Direction | Variable | Fracture median [IQR] | Control median [IQR] | P-value |
|---|---|---|---|---|
| Combined | Angular second moment | 0.002 [0.0009, 0.003] | 0.005 [0.002, 0.009] | 0.047 |
| | Contrast | 42.2 [26.2, 122.9] | 17.7 [12.5, 43.5] | 0.032 |
| | Entropy | 2.8 [2.7, 3.2] | 2.5 [2.2, 2.8] | 0.047 |
| | Inverse difference moment | 0.2 [0.1, 0.2] | 0.3 [0.2, 0.3] | 0.043 |
| Horizontal | Angular second moment | 0.003 [0.001, 0.003] | 0.005 [0.002, 0.01] | 0.061 |
| | Contrast | 30.9 [21.6, 87.4] | 13.5 [9.3, 33.1] | 0.047 |
| | Entropy | 2.7 [2.6, 3.2] | 2.4 [2.2, 2.8] | 0.061 |
| | Inverse difference moment | 0.2 [0.2, 0.3] | 0.3 [0.2, 0.4] | 0.056 |
| Vertical | Angular second moment | 0.002 [0.001, 0.004] | 0.006 [0.003, 0.009] | 0.043 |
| | Contrast | 28.1 [17.4, 88.8] | 12.2 [8.2, 27.8] | 0.025 |
| | Entropy | 2.8 [2.6, 3.2] | 2.4 [2.2, 2.8] | 0.043 |
| | Inverse difference moment | 0.3 [0.2, 0.3] | 0.3 [0.2, 0.4] | 0.03 |
| Left-diagonal | Angular second moment | 0.002 [0.0009, 0.003] | 0.005 [0.002, 0.008] | 0.047 |
| | Contrast | 42.0 [26.5, 114.5] | 18.1 [12.0, 41.8] | 0.022 |
| | Entropy | 2.8 [2.7, 3.3] | 2.5 [2.3, 2.8] | 0.047 |
| | Inverse difference moment | 0.2 [0.1, 0.2] | 0.3 [0.2, 0.3] | 0.047 |
| Right-diagonal | Angular second moment | 0.002 [0.0009, 0.003] | 0.005 [0.002, 0.008] | 0.047 |
| | Contrast | 41.1 [26.1, 110.8] | 17.5 [12.6, 41.0] | 0.027 |
| | Entropy | 2.8 [2.7, 3.2] | 2.5 [2.2, 2.8] | 0.047 |
| | Inverse difference moment | 0.2 [0.1, 0.2] | 0.3 [0.2, 0.3] | 0.043 |
| Through Plane | Angular second moment | 0.002 [0.0007, 0.003] | 0.004 [0.002, 0.007] | 0.036 |
| | Contrast | 66.9 [39.2, 212.8] | 25.6 [20.1, 69.1] | 0.036 |
| | Entropy | 2.9 [2.7, 3.3] | 2.5 [2.3, 2.9] | 0.043 |
| | Inverse difference moment | 0.2 [0.1, 0.2] | 0.2 [0.2, 0.3] | 0.025 |

Figure 3:
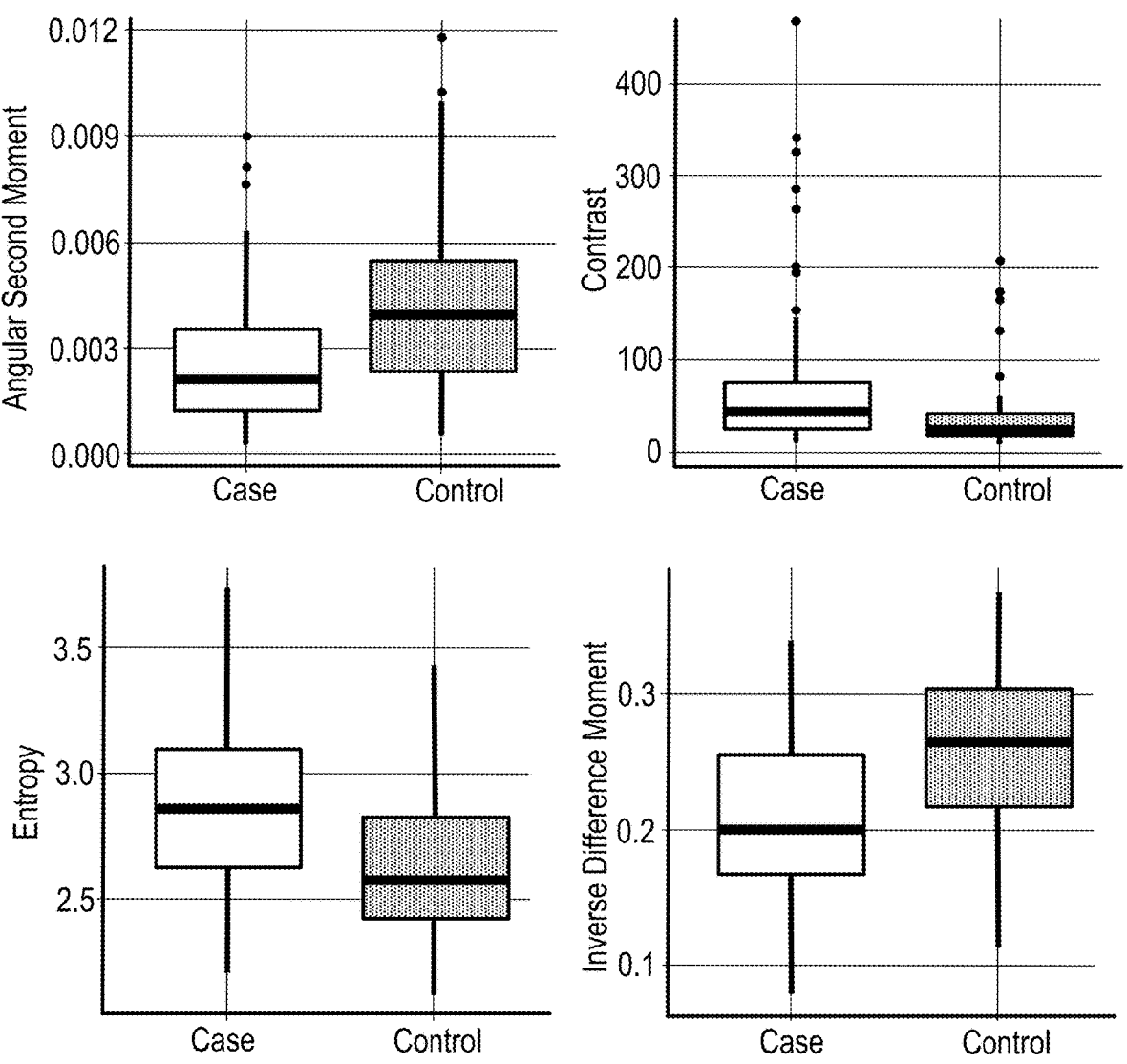
FIG. 3 shows differences in trabecular heterogeneity between subjects with fragility fractures and controls. Box plots show median (horizontal line) and interquartile range for contrast, angular second moment, entropy and inverse difference moment.

In the second study, texture heterogeneity of vertebral trabecular bone (L1-5) was greater among women with fractures. Compared to controls, women with fractures had higher contrast and entropy, measures for which higher values indicate greater heterogeneity. Contrast was 76% greater (p=0.005) and entropy 10% greater (p=0.005) in fracture patients. The mean angular second moment and inverse difference, measures for which lower values indicate greater heterogeneity, were 50% lower (p=0.005) and 22% lower (p=0.003) in fracture patients, respectively (Table 3). FIG. 3 shows box plots indicating the median (horizontal line) and interquartile range for contrast, angular second moment, entropy, and inverse difference moment. There was no significant difference between groups in the correlation texture feature, which is a measure of gray level linear dependence between neighboring pixels.

TABLE 3

Median values for each gray level co-occurrence matrix texture
parameter in combined direction for L1-L5 (second study).

| Variable | Fracture median [IQR] | Control median [IQR] | P-value |
|---|---|---|---|
| Angular second moment | 0.002 [0.001, 0.003] | 0.004 [0.002, 0.006] | <0.01 |

TABLE 3-continued

Median values for each gray level co-occurrence matrix texture
parameter in combined direction for L1-L5 (second study).

| Variable | Fracture median [IQR] | Control median [IQR] | P-value |
|---|---|---|---|
| Contrast | 43.7 [25.5, 74.4] | 23.1 [15.8, 41.9] | <0.01 |
| Correlation | 0.67 [0.64, 0.70] | 0.66 [0.61, 0.69] | 0.34 |
| Entropy | 2.9 [2.6, 3.1] | 2.6 [2.4, 2.8] | <0.01 |
| Inverse difference moment | 0.2 [0.2, 0.3] | 0.3 [0.2, 0.3] | <0.01 |

In the second study, the ability of the texture features to discriminate between fracture and control cases was evaluated using ROC analysis. The area under the curve for most features was 0.69 to 0.70 (Table 4). These features had moderate sensitivity and specificity for fracture; sensitivity ranged from 0.70 to 0.74 for all features except correlation, and specificity from 0.64-0.84.

TABLE 4

Discrimination of fragility by texture variables (second study).
GLCM

| Texture Variable | AUC | (95% CI) | Threshold | Sensitivity | (95% CI) | Specificity | (95% CI) |
|---|---|---|---|---|---|---|---|
| AngScMom | 0.69 | 0.59-0.80 | 0.0029 | 0.70 | 0.58-0.82 | 0.68 | 0.56-0.80 |
| Contrast | 0.69 | 0.59-0.80 | 33.5924 | 0.68 | 0.54-0.80 | 0.68 | 0.56-0.80 |
| Correlat | 0.56 | 0.45-0.67 | 0.6305 | 0.32 | 0.20-0.46 | 0.84 | 0.74-0.94 |
| Entropy | 0.69 | 0.59-0.79 | 2.7192 | 0.70 | 0.28-0.82 | 0.68 | 0.54-0.80 |
| InvDfMom | 0.70 | 0.60-0.80 | 0.2496 | 0.74 | 0.62-0.86 | 0.64 | 0.50-0.78 |

Relationship Between MRI-Based Analysis of Trabecular Bone Heterogeneity and DXA Based TBS In the first study, among the fracture patients, TBS measurements by DXA correlated with MRI based measurements of trabecular bone heterogeneity (Table 5). For the combined directions, there were strong inverse relationships between DXA TBS values and contrast (r=−0.75; p<0.02), and entropy (r=−0.78; p<0.01). There was a direct relationship between DXA TBS and angular second moment (r=0.78; p<0.1). These relationships were observed using the individual anatomic directions as well.

TABLE 5

Correlation Between MRI Based Assessment of
Trabecular Heterogeneity and DXA Based TBS.

| Direction | Variable | Spearman's Correlation Coefficient (95% CI) | p-value |
|---|---|---|---|
| Combined | Angular second moment | 0.78 (0.20, 0.95) | 0.010 |
| | Contrast | −0.75 (−0.94, −0.13) | 0.017 |
| | Entropy | −0.78 (−0.95, −0.20) | 0.010 |
| Horizontal | Angular second moment | 0.77 (0.16, 0.94) | 0.013 |
| | Contrast | −0.77 (−0.94, −0.16) | 0.013 |
| | Entropy | −0.75 (−0.94, −0.13) | 0.017 |
| Vertical | Angular second moment | 0.87 (0.43, 0.97) | 0.001 |
| | Contrast | −0.75 (−0.94, −0.13) | 0.017 |
| | Entropy | −0.80 (−0.95, −0.24) | 0.007 |
| Left-diagonal | Angular second moment | 0.78 (0.20, 0.95) | 0.010 |
| | Contrast | −0.75 (−0.94, −0.13) | 0.017 |
| | Entropy | −0.78 (−0.95, −0.20) | 0.010 |
| Right-diagonal | Angular second moment | 0.78 (0.20, 0.95) | 0.010 |
| | Contrast | −0.75 (−0.94, −0.13) | 0.017 |
| | Entropy | −0.80 (−0.95, −0.24) | 0.007 |
| Through Plane | Angular second moment | 0.78 (0.20, 0.95) | 0.010 |
| | Contrast | −0.75 (−0.94, −0.13) | 0.017 |
| | Entropy | −0.78 (−0.95, −0.20) | 0.010 |

Discussion

In these pilot studies, we investigated an approach for opportunistic screening of MRI scans to identify patients with skeletal fragility. While texture analysis of knee MRI scans has previously been correlated with direct histologic examination in subjects with osteoarthritis, to our knowledge, this is the first description of the application of texture analysis to discriminate patients with skeletal fragility.

Our initial results establish that texture analysis of trabecular bone could be feasibly performed on clinical LS MRI scans. Trabecular bone microarchitectural heterogeneity measured by several independent variables differed in patients with known skeletal fragility and healthy controls. Specifically, fracture patients had higher measurements of local contrast and disorder and lower values of homogeneity. These preliminary results indicate that this opportunistic method has applications for identifying patients with osteoporosis using clinical MRI scans.

As hypothesized, we found that trabecular bone heterogeneity was higher in women with a history of fragility fracture compared to healthy controls measured by several different texture features variables. Angular second motion and inverse difference moment, both measures of homogeneity were lower in fracture cases. Conversely, contrast, a measure of variability, was higher; as was entropy, a measure of disorder. These results suggest that these texture parameters can differentiate patients with skeletal fragility. As our results are not prospective, we cannot discern whether more texturally heterogeneous bone conferred fragility. Increased textural heterogeneity may be related to worse biomechanical properties of bone, as has been shown for trabecular inhomogeneity by HR-pQCT. The specific mechanism by which the measured heterogeneity may result in fragility is an important topic for further investigation.

In the first study, we found that patients who had greater microarchitectural heterogeneity assessed by MRI also had DXA based TBS scores that also reflected more disorderly trabecular distribution (lower TBS). Patients who had more degraded microarchitecture by DXA TBS measurements had higher contrast and entropy. They also had lower angular second moment and inverse difference moment. These relationships suggest that DXA based TBS and MRI based texture analysis may be assessing some similar properties. An advantage of the MRI based analysis is that the direction of the abnormal bone distribution can be considered as another feature contributing to fragility and the mechanism of fracture. We did observe some differences according to direction. While trabecular heterogeneity was greater in fracture patients in all of the anatomic directions assessed, we found the greatest differences compared to controls were in the vertical direction. Given the direction of loading on vertebral bone, specific deficits in the vertical direction may confer a greater risk of vertebral fracture.

In the second study, we found that texture features were able to discriminate fracture in ROC analyses. The AUCs for many of the features including angular second moment, contrast, entropy, and inverse second moment were approximately 0.70. This value is similar to or greater than the ROCs for fracture discrimination based on DXA or high resolution peripheral QCT, as determined in the first study. That AUCs for fracture discrimination are not higher using any of these methods reflects that multiple factors govern fracture risk. Many factors, such as material and mineralization properties of bone, are not measured by these techniques. Importantly, the propensity to fall greatly increases fracture risk and cannot be assessed by any imaging method.

In the second study, our fracture cases and controls were well matched with regard to age and BMI. Groups had similar prevalence of chronic medical conditions and use of medications that may have detrimental effects on bone such as proton pump inhibitors and selective serotonin re-uptake inhibitors. As might be expected, the patients with a history of fragility fracture had higher use of calcium and vitamin D, bisphosphonates, teriparatide and denosumab. Whether these medications affect the texture features we assessed by our method is an important question for future studies.

A strength of the present study is that our assessments were performed using T1 weighted MRI datasets, a sequence that is commonly used to evaluate fatty marrow within trabecular bone. Once further validated, this application could be applied to routine standard of care MRIs without the need for specific image acquisition protocols. This could have broad application to the increasing number of individuals undergoing spine MRIs for indications not related to the assessment of skeletal fragility. Patients found to have higher degrees of trabecular bone heterogeneity could then be referred for dedicated assessment of bone density and quality by more traditional methods, such as DXA.

In conclusion, we found that textural analysis of trabecular bone can be performed on clinical MRI scans and used to discriminate patients with skeletal fragility. Patients with fractures have more trabecular bone microarchitectural heterogeneity as assessed by several different independent measures.

Example Applications

Although the aforementioned techniques were performed with respect to patients having particular characteristics (e.g., Caucasian postmenopausal women), in practice, the aforementioned techniques can be performed with respect to patients having other characteristics (e.g., different genders, ages, ethnicities, or other demographics, and having any other characteristics with respect to their health).

Further, although the aforementioned techniques were performed to analyze particular types of bones (e.g., vertebrae, radii, pelvises, femora, tibiae, ribs, and clavicles), in practice, the aforementioned techniques can be performed to analyze any type of bone. As an example, the aforementioned technique can be performed on any bone that is sufficiently large (e.g., sufficiently long or wide with respect to one or more dimensions).

Further, the aforementioned techniques can be performed using one or more image texture metrics (e.g., one or more metrics indicating a heterogeneity of an image). As examples, as described above, the health of a patient's bones and/or risks associated with the patient (e.g., bone fracture risk) can be determined based on an angular second moment, an entropy, contrast, and/or an inverse difference moment, other individual texture features, or a combined Bone Texture Index, associated with MRI images of the patient's bones. As further examples, the health of a patient's bones and/or risks associated with the patient can be determined based on other metrics regarding an image, such as energy, contrast, homogeneity, autocorrelation, correlation, cluster shade, histogram, mean, variance, skewness, absolute gradient, gradient mean, gradient variance, gradient skewness, gradient kurtosis, gradient non-zeros (e.g., the proportion of pixels with non-zero gradient), run length matrix, short run length matrix, long run length matrix, run length non-uniformity, gray level non-uniformity, and/or fraction runs (e.g., the fraction of gray values occurring in runs). Further, the analysis can be performed based on a linear or non-linear combination of one or more of the aforementioned metrics, as well as the second or higher order interactions between them, or based on a combination that produces a Bone Texture Index.

Further, each of the metrics can be determined with respect to one or more different directions. For example, at least some of the metrics can be determined according to a vertical direction, a horizontal direction, a through plane direction, a left-diagonal direction, and/or a right-diagonal direction, or a combination thereof. As another example, at least some of the metrics can be determined according to diagonal directions expressed according to a cubic kernel. For example, given a cubic kernel, one such diagonal would run from the top, left, front corner to the back, right, bottom corner. There are four such unique diagonals. Further, the analysis can be performed based on a linear or non-linear combination of one or more of the aforementioned directions, as well as the second or higher order interactions between them.

In some implementation, a Bone Texture Index can be calculated based on multiple different metrics in combination with one another (e.g., any combination of the metrics described herein). As an example, a Bone Texture Index of a particular patient can have a numerical value that depends on an angular second moment, an entropy, contrast, an inverse difference moment, and/or any of the metrics described herein, calculated using one or more MRI images of the subject's bones.

In some implementations, the Bone Texture Index can be a weighted sum of multiple metrics. For example, the Bone Texture Index can be calculated using the function:

$$BTI = w_1 x_1 + w_2 x_2 + \ldots + w_n x_n,$$

where BTI is the Bone Texture Index, $x_i$ is a texture metric (e.g., as described herein), and $w_i$ is a weighting coefficient for that texture metric. In some implementations, the weighting coefficients can be determined empirically (e.g., by performing experiments to determine the relative weight of each texture metric in determining a health of a patient's bone and/or a risk associated with the patient's bone).

In the example function above, the Bone Texture Index is calculated based on a weighted sum of multiple metrics (e.g., a linear combination of metrics). However, in practice, the Bone Texture Index can also be calculated based on a non-linear combination of metrics.

Example Process

FIG. 4 shows an example process 400 for determining a bone risk or a bone health of the patient using MRI. In some implementations, the process 400 can be performed, at least in part, using a computer system (e.g., the computer system 500 shown in FIG. 5).

According to the process 400, a computer system receives one or more images of one or more bones of a patient (block 402). The one or more images are generated by a magnetic resonance imaging (MRI).

In some implementations, the one or more bones can include trabecular bone or cancellous bone (e.g., porous bone composed of trabeculated bone tissue). For example, the one or more bones can include at least one of a vertebra, a radius, a pelvis, a femur, a tibia, a rib, or a clavicle.

The computer system determines one or more metrics indicative of an image texture of the one or more images (block 404).

In some implementations, determine one or more metrics indicative of the image texture of the one or more images can include determining a heterogeneity of the one or more images.

In some implementations, the one or more metrics can include any combination of an inverse difference moment associated with the one or more images, an angular second moment associated with the one or more images, an entropy associated with the one or more images, an energy of the one or more images, a contrast of the one or more images, a homogeneity of the one or more images, an autocorrelation of the one or more images, a correlation of the one or more images, a cluster shade of the one or more images, a histogram of the one or more images, a mean of the one or more images, a variance of the one or more images, a skewness of the one or more images, an absolute gradient of the one or more images, a gradient mean of the one or more images, a gradient variance of the one or more images, a gradient skewness of the one or more images, a gradient kurtosis of the one or more images, a proportion of pixels with non-zero gradient of the one or more images, a run length matrix of the one or more images, a short run length matrix of the one or more images, a long run length matrix of the one or more images, a run length non-uniformity of the one or more images, a gray level non-uniformity of the one or more images, and/or fraction run of the one or more images.

In some implementations, each of the one or more metrics can be associated with a spatial direction. In some implementations each of the one or more metrics can be associated with a plurality of spatial directions. In some implementations, each of the spatial directions can be a respective diagonal direction expressed according to a cubic kernel. In some implementations the plurality of spatial directions can include four diagonal directions expressed according to a cubic kernel.

The computer system determines at least one of a bone risk or a bone health of the patient based on the one or more metrics (block 406).

In some implementations, determining the bone risk and/or the bone health of the patient can include determining a bone fracture risk for the patient, determining a disorder associated with the one or more bones, determining that patient suffers from osteoporosis, determining a risk of complications associated an orthopedic procedure, and/or determining a likelihood of success associated with an orthopedic procedure.

In some implementations, the computer system can determine a plurality of first metrics indicative of the image texture of the one or more images. As an example, the first metrics can include any combination of the metrics described above. Further, the computer system can determine, based on the plurality of first metrics, a second metric indicative of at least one of the bone risk or the bone health of the patient. As an example, the second metric can be a Bone Texture Index, as described above.

In some implementations, the second metric can be a weighted sum of the plurality of first metrics. In some implementations, the second metric can be a linear combination of the plurality of first metrics. In some implementations, the second metric can be a non-linear combination of the plurality of first metrics.

Example Systems

Some implementations of subject matter and operations described in this specification can be implemented in digital electronic circuitry, or in computer software, firmware, or hardware, including the structures disclosed in this specification and their structural equivalents, or in combinations of one or more of them.

Some implementations described in this specification can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 5:
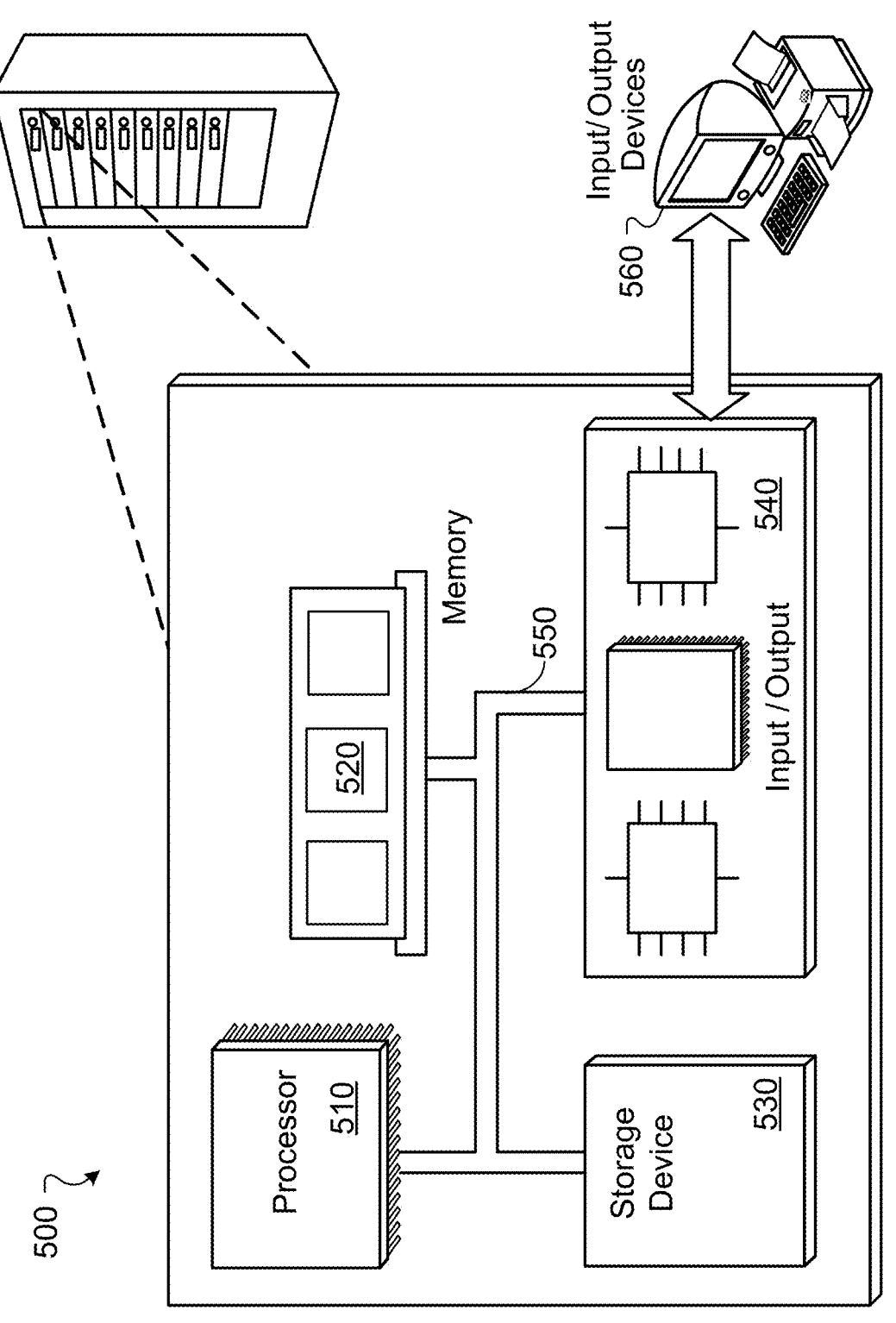
FIG. 5 is a schematic diagram of an example computer system.

FIG. 5 shows an example computer system 500 that includes a processor 510, a memory 520, a storage device 530 and an input/output device 440. Each of the components 510, 520, 530 and 540 can be interconnected, for example, by a system bus 550. The processor 510 is capable of processing instructions for execution within the system 500. In some implementations, the processor 510 is a single-threaded processor, a multi-threaded processor, or another type of processor. The processor 510 is capable of processing instructions stored in the memory 520 or on the storage device 530. The memory 520 and the storage device 530 can store information within the system 500.

The input/output device 540 provides input/output operations for the system 500. In some implementations, the input/output device 540 can include one or more of a network interface device, e.g., an Ethernet card, a serial communication device, e.g., an RS-232 port, and/or a wireless interface device, e.g., an 802.11 card, a 3G wireless modem, a 4G wireless modem, a 5G wireless modem, etc. In some implementations, the input/output device can include driver devices configured to receive input data and send output data to other input/output devices, e.g., keyboard, printer and display devices 560. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of implementations have been described. Nevertheless, it will be understood that various modifications may be made without departing from the spirit and scope of the invention. Accordingly, other implementations are within the scope of the following claims.

The invention claimed is:

1. A method comprising:
   receiving, by a computer system, one or more images of one or more bones of a patient, wherein the one or more images are generated by a magnetic resonance imaging (MRI);

determining, by the computer system, a plurality of first metrics indicative of an image texture of the one or more images, wherein the plurality of first metrics comprises:
   an inverse difference moment associated with the one or more images, wherein the inverse difference moment is associated with a plurality of spatial directions,
   an angular second moment of the one or more images,
   a contrast of the one or more images, and
   an entropy associated with the one or more images;
determining, by the computer system, at least one of a bone risk or a bone health of the patient based on the plurality of first metrics, wherein determining the bone health of the patient comprises determining a second metric that indicates at least one of (i) whether the patient suffers from osteoporosis or (ii) a bone fracture risk for the patient, wherein the second metric is a weighted sum of the plurality of first metrics,
wherein the weighted sum of the plurality of first metrics comprises:
   a first term representing a first weight multiplied by the inverse difference moment associated with the one or more images,
   a second term representing a second weight multiplied by the angular second moment of the one or more images,
   a third term representing a third weight multiplied by the contrast of the one or more images,
   a fourth term representing a fourth weight multiplied by the entropy associated with the one or more images, and
wherein determining the second metric comprises summing at least the first term, second term, third term, and fourth term.

2. The method of claim 1, wherein the one or more bones comprise trabecular bone.

3. The method of claim 1, wherein the one or more bones comprise at least one of a vertebra, a radius, a pelvis, a femur, a tibia, a rib, or a clavicle.

4. The method of claim 1, wherein determining at least one of the bone risk or the bone health of the patient comprises:
   determining the bone fracture risk for the patient.

5. The method of claim 1, wherein determining at least one of the bone risk or the bone health of the patient comprises:
   determining a disorder associated with the one or more bones.

6. The method of claim 1, wherein determining at least one of the bone risk or the bone health of the patient comprises:
   determining that patient suffers from osteoporosis.

7. The method of claim 1, wherein determining at least one of the bone risk or the bone health of the patient comprises:
   determining a risk of complications associated an orthopedic procedure.

8. The method of claim 1, wherein determining at least one of the bone risk or the bone health of the patient comprises:
   determining a likelihood of success associated with an orthopedic procedure.

9. The method of claim 1, wherein determining the one or more first metrics indicative of the image texture of the one or more images comprises:
   determining a heterogeneity of the one or more images.

10. The method of claim 1, wherein the plurality of first metrics further comprises at least one of:
- an energy of the one or more images,
- a homogeneity of the one or more images,
- an autocorrelation of the one or more images,
- a correlation of the one or more images,
- a cluster shade of the one or more images,
- a histogram of the one or more images,
- a mean of the one or more images,
- a variance of the one or more images,
- a skewness of the one or more images,
- an absolute gradient of the one or more images,
- a gradient mean of the one or more images,
- a gradient variance of the one or more images,
- a gradient skewness of the one or more images,
- a gradient kurtosis of the one or more images,
- a proportion of pixels with non-zero gradient of the one or more images,

- a run length matrix of the one or more images,
- a short run length matrix of the one or more images,
- a long run length matrix of the one or more images,
- a run length non-uniformity of the one or more images,
- a gray level non-uniformity of the one or more images, or
- fraction run of the one or more images.

11. The method of claim 1, wherein each of the plurality of first metrics is associated with a plurality of spatial directions.

12. The method of claim 11, wherein each of the spatial directions is a respective diagonal direction expressed according to a cubic kernel.

13. The method of claim 11, wherein the plurality of spatial directions comprise four diagonal directions expressed according to a cubic kernel.

\* \* \* \* \*